(12) United States Patent
Closson et al.

(10) Patent No.: US 8,080,691 B2
(45) Date of Patent: *Dec. 20, 2011

(54) ORGANOLEPTIC COMPOUNDS

(75) Inventors: Adam P. Closson, Red Bank, NJ (US);
Michael G. Monteleone, Hazlet, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/908,038

(22) Filed: Oct. 20, 2010

(65) Prior Publication Data

US 2011/0034736 A1 Feb. 10, 2011

Related U.S. Application Data

(63) Continuation-in-part of application No. 12/692,682, filed on Jan. 25, 2010, now Pat. No. 7,842,659, which is a continuation-in-part of application No. 11/958,038, filed on Dec. 17, 2007, now Pat. No. 7,678,749.

(51) Int. Cl.
*C07C 49/323* (2006.01)
(52) U.S. Cl. .................................... 568/374
(58) Field of Classification Search ............... 568/374
See application file for complete search history.

(56) References Cited

OTHER PUBLICATIONS

Lewis N. Mander "The Chemistry of Gibberellins: An Overview" Chem. Rev. (1992) 92, pp. 573-612.
Hiromitsu Nakajima et al. "Sorokinianin: A novel phytotoxin produced by the phytopathogenic fungus *Bipolaris sorokiniana*" Tetr. Lett. (1994) 35(51), pp. 9597-9600.
Winfred G. Beyersbergen van Henegouwen et al. "Studies toward the Total Synthesis of the Oxindole Alkaloid Gelsedine: An Efficient Allene-Terminated N-Acyliminium Ion Cyclization" J. Org. Chem. (1997) 62(25), pp. 8862-8867.
Xing Dai et al. "Formal Enantioselective [4 + 3] Cycloaddition by a Tandem Diels-Alder Reaction/Ring Expansion" Adv. Synth. Catal. (2006) 348(16-17), pp. 2449-2456.

*Primary Examiner* — John Hardee
(74) *Attorney, Agent, or Firm* — Elizabeth M. Quirk; XuFan Tseng; Joseph F. Leightner

(57) ABSTRACT

The present invention is directed to novel fragrance compounds and their unexpected advantageous use in enhancing, improving or modifying a fragrance formulation through the addition of an olfactory acceptable amount of the compounds, wherein the compounds are represented by the following formula:

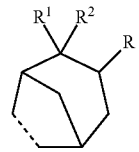

wherein the dotted line represents a single or double bond;
R is selected from the group consisting of propyl, butyl, and pentyl; and
$R^1$ and $R^2$ together represent =O or a ring structure represented by

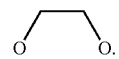

2 Claims, No Drawings

ORGANOLEPTIC COMPOUNDS

STATUS OF RELATED APPLICATIONS

This application is a continuation-in-part of U.S. Ser. No. 12/692,682, filed Jan. 25, 2010, now U.S. Pat. No. 7,842,659, which is a continuation-in-part of U.S. Ser. No. 11/958,038, filed Dec. 17, 2007, now U.S. Pat. No. 7,678,749, the contents hereby incorporated by references as if set forth in their entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how small differences in chemical structures can result in unexpected and significant differences in odor, notes and characteristics of molecules. These variations allow perfumers and other persons to apply new compounds in creating new fragrances.

The synthesis of natural bicycle[3.2.1]octane products has been previously reported. The interest is driven by the biological activities that some of these natural products display. The major function has been shown in plant growth and development, and these products may also provide some medicinal benefits. However, the chemistry of natural bicycle [3.2.1]octane products is rich and diverse, no further properties of any of these natural products were reported [Mander, Chem. Rev. 92: 573-612 (1992); Nakajima et al., Tetr. Lett. 35(51): 9597-9600 (1994); Beyersbergen van Henegouwen et al., J. Org. Chem. 62(25): 8862-8867 (1997); Dai et al., Adv. Synth. Catal. 348(16-17): 2449-2456 (2006)].

SUMMARY OF THE INVENTION

The present invention provides novel chemicals and their unexpected advantageous use in enhancing, improving or modifying the fragrance of perfumes, colognes, toilet waters, personal products, fabric care products, and the like.

One embodiment of the present invention is directed to a novel fragrance compound represented by the following formula:

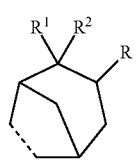

Structure I wherein the dotted line represents a single or double bond;

R is selected from the group consisting of propyl, butyl, and pentyl; and $R^1$ and $R^2$ together represent =O or a ring structure represented by

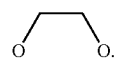

Another embodiment of the present invention is directed to a novel fragrance compound that exhibits unexpected strong fragrance effect, whereby the fragrance compound is represented by the following formula:

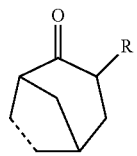

Structure II wherein the dotted line and R are defined as above.

Another embodiment of the present invention is directed to the use of the compounds provided above as fragrance materials in perfumes, colognes, toilet waters, personal products, fabric care products, and the like.

Another embodiment of the present invention is directed to a fragrance composition comprising the compounds provided above.

Another embodiment of the present invention is directed to a fragrance product comprising the compounds provided above.

Another embodiment of the present invention is directed to a method of improving, enhancing or modifying a fragrance formulation by incorporating an olfactory acceptable amount of the compounds provided above.

These and other embodiments of the present invention will be apparent by reading the following specification.

DETAILED DESCRIPTION OF THE INVENTION

It has been surprisingly found that the compounds of the present invention provide unexpected strong green and herbal characteristics.

In one embodiment of the present invention, the compounds of the present invention are represented by the following structures:

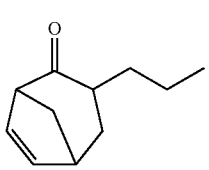

Structure III

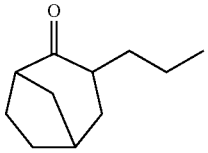

Structure IV

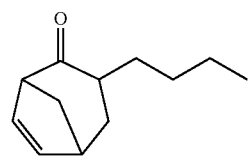

Structure V

-continued

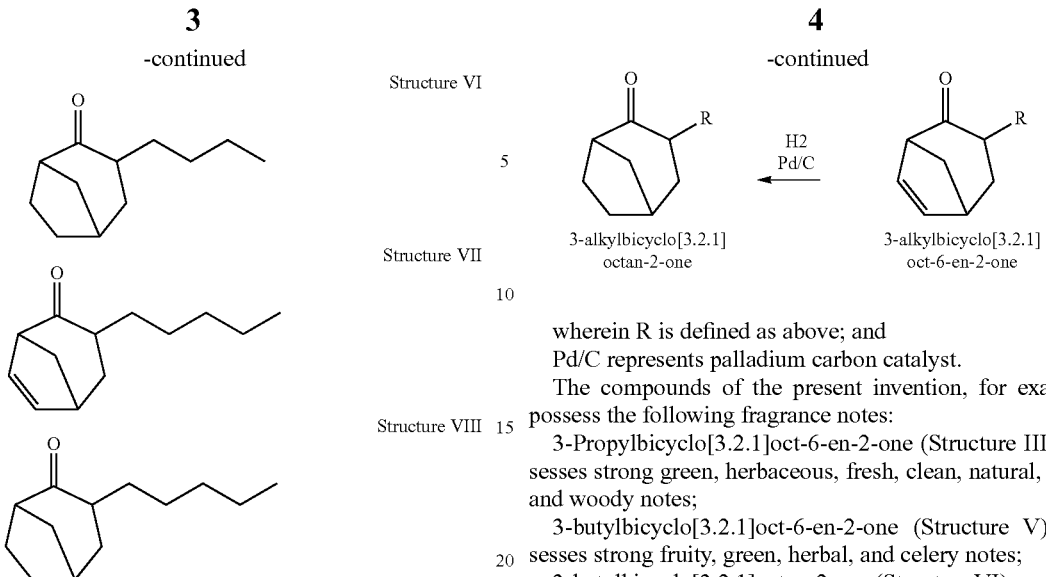

Those with skill in the art will recognize that:
Structure III is 3-propylbicyclo[3.2.1]oct-6-en-2-one;
Structure IV is 3-propylbicyclo[3.2.1]octan-2-one;
Structure V is 3-butylbicyclo[3.2.1]oct-6-en-2-one;
Structure VI is 3-butylbicyclo[3.2.1]octan-2-one;
Structure VII is 3-pentylbicyclo[3.2.1]oct-6-en-2-one; and
Structure VIII is 3-pentylbicyclo[3.2.1]octan-2-one.

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

The compounds of the present invention were prepared with corresponding aldehydes according to the following reaction schemes, the details of which are specified in the Examples. The starting materials and catalysts were purchased from Aldrich Chemical Company.

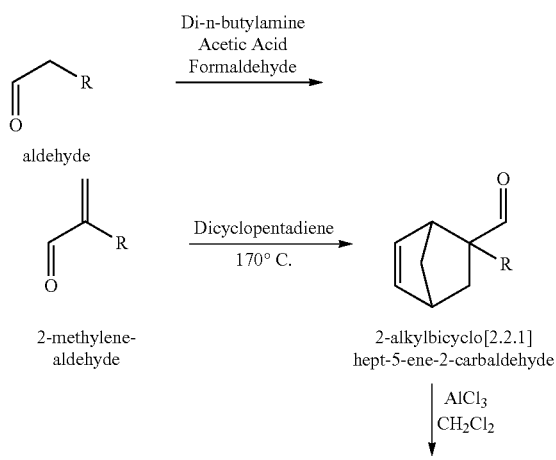

wherein R is defined as above; and
Pd/C represents palladium carbon catalyst.

The compounds of the present invention, for example, possess the following fragrance notes:

3-Propylbicyclo[3.2.1]oct-6-en-2-one (Structure III) possesses strong green, herbaceous, fresh, clean, natural, floral, and woody notes;

3-butylbicyclo[3.2.1]oct-6-en-2-one (Structure V) possesses strong fruity, green, herbal, and celery notes;

3-butylbicyclo[3.2.1]octan-2-one (Structure VI) possesses strong coconut, lactonic, woody, minty, jasmine cis like, anisic, and tuberose notes;

3-pentylbicyclo[3.2.1]oct-6-en-2-one (Structure VII) possesses strong anisic, fruity, spicy, mossy, herbal, and celery notes; and 3-pentylbicyclo[3.2.1]octan-2-one (Structure VIII) possesses strong sweet, slight anisic, floral, and celery notes.

The use of the compounds of the present invention is widely applicable in current perfumery products, including the preparation of perfumes and colognes, the perfuming of personal care products such as soaps, shower gels, and hair care products, fabric care products as well as air fresheners and cosmetic preparations. These compounds can also be used to perfume cleaning agents, such as, but not limited to detergents, dishwashing materials, scrubbing compositions, window cleaners and the like. In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk; and flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The terms "fragrance formulation", "fragrance composition", and "perfume composition" are understood to mean the same and refer to a formulation that is intended for providing a fragrance character to a perfume, a cologne, toilet water, a personal product, a fabric care product, and the like. The fragrance formulation of the present invention is a composition comprising a compound of the present invention.

Olfactory acceptable amount is understood to mean the amount of a compound in a perfume composition. The compound will contribute its particular olfactory characteristics, but the olfactory effect of the perfume composition will be the sum of the effects of each of the perfumes or fragrance ingredients. Thus the compounds of the invention can be used to alter the aroma characteristics of a perfume composition, or by modifying the olfactory reaction contributed by another ingredient in the composition. The amount will vary depending on many factors including other ingredients, their relative amounts and the effect that is desired.

The amount of the compounds of the present invention employed in a fragrance formulation varies from about 0.005 to about 70 weight percent, preferably from 0.005 to about 10 weight percent, more preferably from about 0.5 to about 8 weight percent, and even more preferably from about 1 to about 7 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation this ingredient provides green and herbal notes that make the fragrance formulation more desirable and noticeable and add the perception of value. All of the odor qualities found in this material assist in beautifying and enhancing the finished accord improving the performance of the other materials in the fragrance. There is also the fruity side of it which is found in many fragrances today which happens to be very trendy, especially for the younger consumers.

The following are provided as specific embodiments of the present invention. Other modifications of this invention will be readily apparent to those skilled in the art. Such modifications are understood to be within the scope of this invention. The chemical materials used in the preparation of the compounds of the present invention are commercially available from Aldrich Chemical Company. As used herein all percentages are weight percent unless otherwise noted, ppm is understood to stand for parts per million, L is understood to be liter, mL is understood to be milliliter, Kg is understood to be kilogram, and g be gram. IFF as used in the examples is understood to mean International Flavors & Fragrances Inc., New York, N.Y., USA.

Example I

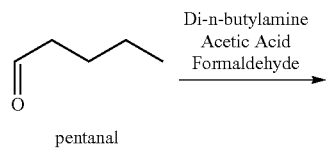

pentanal

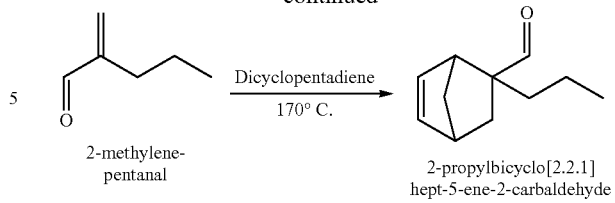

2-methylene-pentanal 2-propylbicyclo[2.2.1]hept-5-ene-2-carbaldehyde

Preparation of 2-Propylbicyclo[2.2.1]hept-5-ene-2-carbaldehyde: A 5-L flask fitted with an overhead stirrer and a condenser was charged with di-n-butylamine (75 g) and acetic acid (70 g). Formaldehyde solution in water (1.3 L, 37%) was added and the resulting solution was heated to 50° C. with stirring. Pentanal (1 Kg) was then fed in over about 2 hours. After the feed was completed the temperature was maintained at 50° C. for 1 hour and then cooled to room temperature. The reaction mixture was poured into a separatory funnel. The organic layer was washed with water and purified by distillation to yield 2-methylene pentanal (820 g).

2-Methylene pentanal (302 g) and dicyclopentadiene (244 g) were loaded into a 2-L autoclave. The autoclave was sealed and heated to 170° C. The reaction was monitored by Gas Chromatography ("GC") analysis, which showed the completion after 3 hours. The reaction was cooled to room temperature. The crude product was purified by distillation to yield 2-propylbicyclo[2.2.1]hept-5-ene-2-carbaldehyde (136 g).

Product 2-methylene pentanal had the following NMR spectral characteristics:

$^1$H NMR (CDCl$_3$, 500 MHz): 0.90 ppm (t, 3H, J=7 Hz), 1.48 ppm (q, 2H, J=7.5 Hz), 2.22 ppm (t, J=7.5 Hz), 5.99 ppm (s, 1H), 6.24 ppm (s, 1H), 9.54 ppm (s, 1H).

Product 2-propylbicyclo[2.2.1]hept-5-ene-2-carbaldehyde had the following NMR spectral characteristics:

$^1$H NMR (CDCl$_3$, 500 MHz): 0.84 ppm (t, 3H, J=7.2 Hz), 1.11-1.39 ppm (m, 6H), 1.49-1.57 ppm (m, 1H), 2.16 ppm (m, 1H), 2.85 ppm (s, 1H), 2.93 ppm (s, 1H), 6.07 ppm (dd, 1H, J=5.37, 3.13 Hz), 6.27 ppm (dd, 1H, J=5.33, 3.08 Hz), 9.70 ppm (s, 1H).

Example II

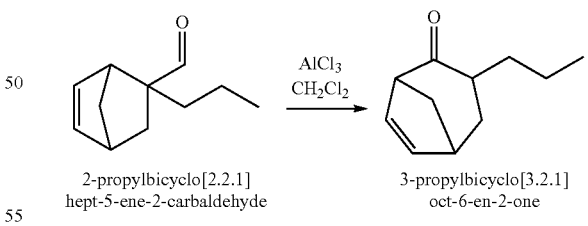

2-propylbicyclo[2.2.1]hept-5-ene-2-carbaldehyde 3-propylbicyclo[3.2.1]oct-6-en-2-one Preparation of 3-Propylbicyclo[3.2.1]oct-6-en-2-one (Structure III): Aluminum chloride (AlCl$_3$, 110 g) was suspended in toluene (1 L) and chilled to −30° C. using a dry ice/isopropanol bath. 2-Propylbicyclo[2.2.1]hept-5-ene-2-carbaldehyde (136 g, synthesized as above) was fed in using an addition funnel over 1 hour while the temperature was maintained at −30° C. After the feed was completed the temperature was allowed to rise to 0° C. GC analysis showed the reaction was completed after 40 minutes. The reaction mixture was then poured onto H$_2$SO$_4$ (1 L, 20%) over ice. The resulting biphasic mixture was shaken to split the organic and aqueous layers. The aqueous layer was washed once with toluene (300 mL) and combined with the organic layers. The mixture was then washed with NaOH solution (750 mL, 10%), followed by water until the water was tested neutral. The resulting organic material was purified by distillation to yield 3-propylbicyclo[3.2.1]oct-6-en-2-one (92 g).

$^1$H NMR (CDCl$_3$, 500 MHz): 0.87 ppm (t, 3H, J=7.2 Hz), 1.16-1.37 ppm (m, 3H), 1.44-1.50 ppm (m, 1H), 1.72-1.81 ppm (m, 1H), 1.83-2.00 ppm (m, ⅔H), 2.12-2.4 ppm (m, 2H), 2.38-2.52 ppm (m, 1H), 2.64-2.70 ppm (m, ⅓H), 2.77-2.86 (m, 1H), 3.00-3.06 ppm (m, 1H), 5.80 ppm (dd, ⅔H, J=5.4, 3.1 Hz), 6.05 ppm (dd, ⅓H, J=5.7, 2.9 Hz), 6.21-6.26 ppm (m, 1H).

3-Propylbicyclo[3.2.1]oct-6-en-2-one, possessed strong green, herbaceous, fresh, clean, natural, floral, and woody notes.

Example III

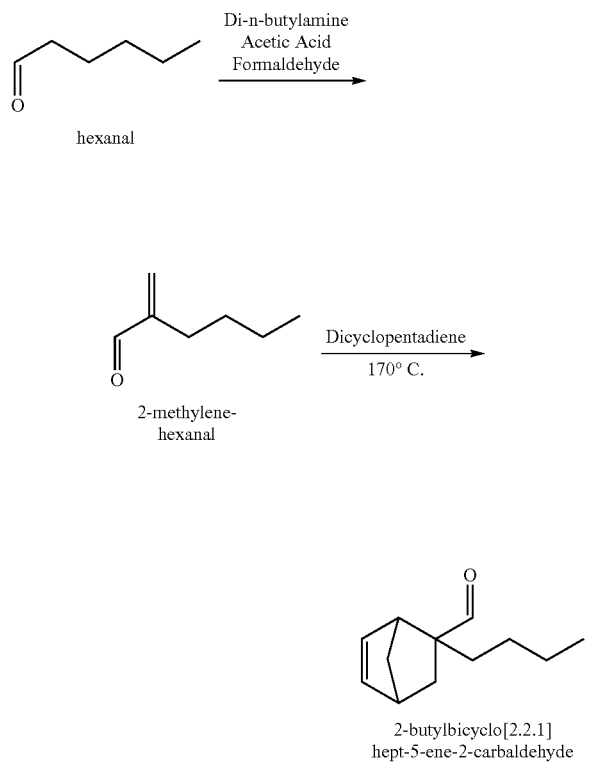

Preparation of 2-Butylbicyclo[2.2.1]hept-5-ene-2-carbaldehyde: A 5-L flask fitted with an overhead stirrer and a condenser was charged with di-n-butylamine (77 g) and acetic acid (72 g). Formaldehyde solution in water (1.1 L, 37%) was added and the resulting solution was heated to 50° C. with stirring. Hexanal (1 Kg) was then fed in over about 2 hours. After GC analysis showed the completion of the reaction, the reaction mixture was cooled to room temperature, poured into a separatory funnel, and washed once with HCl solution (5%). The organic layer was then washed with saturated sodium bicarbonate to provide crude 2-methylene hexanal (727 g), which was loaded into a 2-L stainless steel pressure reactor along with dicyclopentadiene (511 g). The pressure reactor was sealed and heated to 170° C. with stirring for two hours. The reaction was then cooled to room temperature. The resulting crude product was purified by distillation to yield 2-butylbicyclo[2.2.1]hept-5-ene-2-carbaldehyde (570 g).

Example IV

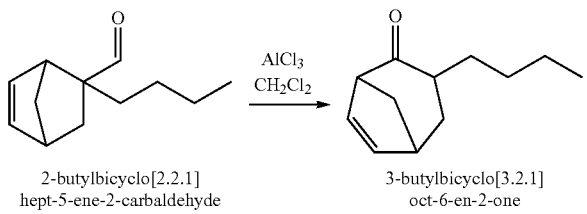

Preparation of 3-Butylbicyclo[3.2.1]oct-6-en-2-one (Structure V): 2-Butylbicyclo[2.2.1]hept-5-ene-2-carbaldehyde (570 g, synthesized as above) was loaded into a 3-L round bottom flask fitted with an overhead stirrer and a condenser, followed by methylene chloride (CH$_2$Cl$_2$, 1 L). The resulting solution was cooled to −50° C. using a dry ice bath. Anhydrous aluminum chloride (AlCl$_3$, 215 g) was then added in one portion. The light yellow solution changed color to orange, then dark red with a simultaneous increase in reaction temperature, up to about −30° C. The reaction temperature was allowed to gradually increase to 15° C. GC analysis showed the completion of the reaction after 1 hour. The reaction mixture was then poured onto ice and sulfuric acid (10%), and the organic layers were separated and washed once with sodium hydroxide solution (10%). The solvent (CH$_2$Cl$_2$) was removed under reduced pressure, and the resulting crude product was purified by distillation to yield 2-butylbicyclo[2.2.1]oct-6-en-2-one (224 g).

$^1$H NMR (CDCl$_3$, 500 MHz): 0.88 ppm (t, 3H, J=7.03 Hz), 1.18-1.38 ppm (m, 5H+~20% of 1H), 1.44-1.50 ppm (m, ~80% of 1H), 1.75-1.85 (m, ~80% of 1H), 1.84 ppm (d, 1H, J=11.1 Hz), 1.94-1.99 ppm (m, ~80% of 1H), 2.12-2.25 ppm (m, ~20% of 3H), 2.39-2.52 (m, 1H), 2.64-2.71 (m, ~80% of 1H), 2.77-2.88 ppm (m, 1H), 3.00-3.07 ppm (m, 1H), 5.78-5.82 ppm (m, ~20% of 1H), 6.02-6.07 ppm (dd, ~80% of 1H, J=5.29, 2.82 Hz), 6.19-6.28 ppm (dd, 1H, J=5.55, 2.65 Hz).

3-Butylbicyclo[3.2.1]oct-6-en-2-one possessed strong fruity, green, herbal, and celery notes.

Example V

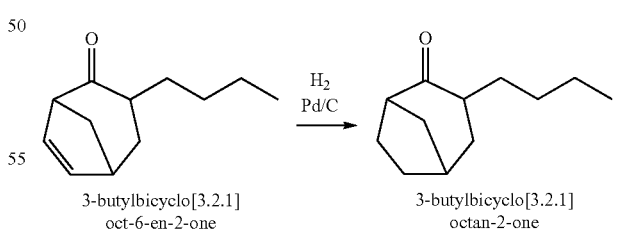

Preparation of 3-Butylbicyclo[3.2.1]octan-2-one (Structure VI): 3-Butylbicyclo[3.2.1]oct-6-en-2-one (100 g, synthesized as above) was placed in a stainless steel autoclave with isopropanol (50 g) and palladium on carbon (Pd/C, 1 g). The mixture was placed under 300 psi of hydrogen gas (H$_2$) and heated at 100° C. until gas uptake ceased. The resulting material was removed from the autoclave, filtered, and distilled to yield 3-butylbicyclo[3.2.1]octan-2-one (55 g).

$^1$H NMR (CDCl$_3$, 500 MHz): 0.99 ppm (t, 3H, J=7.11 Hz), 1.11-1.34 ppm (m, 6H), 1.65-1.75 ppm (m, 3H), 1.76-1.88 ppm (m, 3H), 1.90-2.02 ppm (m, 2H), 2.24-2.34 ppm (m, 1H), 2.39-2.44 ppm (m, 1H), 2.70-2.74 ppm (m, 1H).

3-Butylbicyclo[3.2.1]octan-2-one possessed strong coconut, lactonic, woody, minty, jasmine cis like, anisic, and tuberose notes.

Example VI

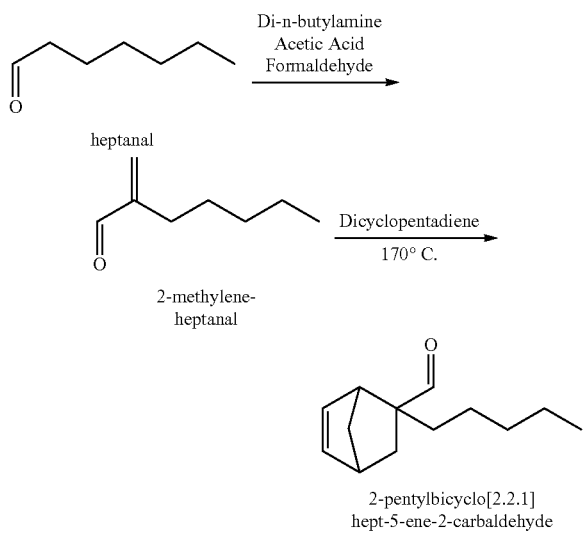

2-pentylbicyclo[2.2.1]
hept-5-ene-2-carbaldehyde

Preparation of 2-Pentylbicyclo[2.2.1]hept-5-ene-2-carbaldehyde: A 3-L three-neck flask fitted with an overhead stirrer and a condenser was charged with di-n-butylamine (33 g) and acetic acid (31 g). Formaldehyde solution in water (500 mL, 33%) was added and the resulting solution was heated to 50° C. with stirring. Heptanal (500 g) was fed in over about 1.5 hours. A slight exotherm was noticed during the feed. GC analysis showed the consumption of heptanal and the production of 2-methylene heptanal, and a conversion rate of about 95% after the feed was completed. The reaction was cooled to room temperature and the reaction mixture was poured into a separatory funnel and washed once with HCl solution (5%). The organic layer was then washed once with saturated sodium carbonate to provide crude 2-methylene heptanal (553 g), which was loaded into a 2-L stainless steel pressure reactor along with dicyclopentadiene (343 g). The pressure reactor was sealed and heated to 170° C. with stirring for two hours. The reaction was then cooled to room temperature. The resulting crude product was purified by distillation to yield 2-pentylbicyclo[2.2.1]hept-5-ene-2-carbaldehyde (217 g).

Example VII

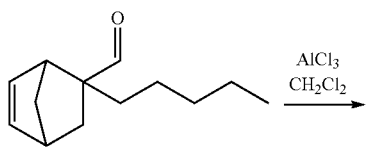

2-pentylbicyclo[2.2.1]
hept-5-ene-2-carbaldehyde

AlCl$_3$
CH$_2$Cl$_2$

-continued

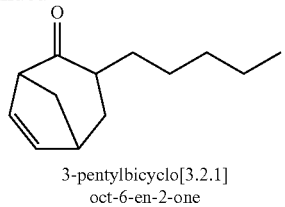

3-pentylbicyclo[3.2.1]
oct-6-en-2-one

Preparation of 3-Pentylbicyclo[3.2.1]oct-6-en-2-one (Structure VII): 2-Pentylbicyclo[2.2.1]hept-5-ene-2-carbaldehyde (217 g, synthesized as above) was loaded into a 2-L round bottom flask fitted with an overheard stirrer and a condenser, followed by CH$_2$Cl$_2$ (1 L). The resulting mixture was cooled to 0° C. using a dry ice bath. AlCl$_3$ (153 g) was then added in one portion. After GC analysis showed the completion of the reaction, the reaction mixture was poured onto ice, and the organic layers were separated and washed once with sodium hydroxide solution (10%). The solvent (CH$_2$Cl$_2$) was then removed under reduced pressure, and the resulting crude product was purified by distillation to yield 3-pentylbicyclo[3.2.1]oct-6-en-2-one (100 g).

$^1$H NMR (CDCl$_3$, 500 MHz): 0.87 ppm (t, 3H, J=7.05 Hz), 1.16-1.36 ppm (m, 8H), 1.76-1.83 ppm (m, 1H), 2.11-2.24 ppm (m, 3H), 2.44-2.50 ppm (m, 1H), 2.78 (s, 1H), 3.05 ppm (t, 1H, J=3.69 Hz), 5.80 ppm (dd, 1H, J=5.12, 3.31 Hz), 6.24 (dd, 1H, J=5.29, 2.91 Hz).

3-Pentylbicyclo[3.2.1]oct-6-en-2-one possessed strong anisic, fruity, spicy, mossy, herbal, and celery notes.

Example VIII

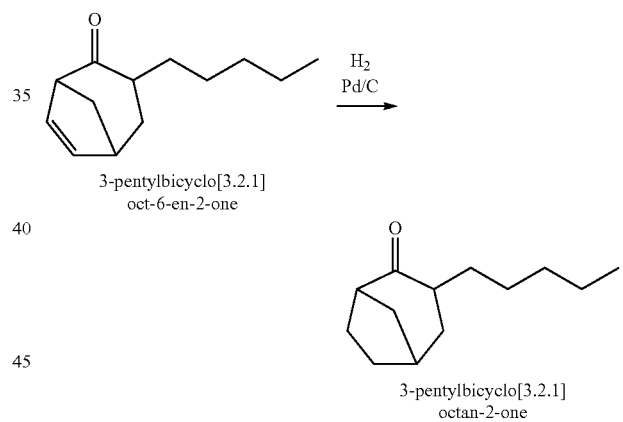

Preparation of 3-Pentylbicyclo[3.2.1]octan-2-one (Structure VIII): 3-Pentylbicyclo[3.2.1]oct-6-en-2-one (130 g, synthesized as above) was placed in a stainless steel autoclave with isopropanol (30 g) and Pd/C (1.5 g). The mixture was placed under 300 psi of hydrogen gas, and heated at 100° C. until gas uptake ceased. The resulting material was then removed from the autoclave, filtered, and distilled to yield 3-pentylbicyclo[3.2.1]octan-2-one 70 g).

$^1$H NMR (CDCl$_3$, 500 MHz): 0.88 ppm (t, 3H, J=6.89 Hz), 1.10-1.18 ppm (m, 1H), 1.19-1.37 ppm (m, 7H), 1.65-1.89 ppm (m, 6H), 1.90-2.03 ppm (m, 2H), 2.25-2.34 ppm (m, 1H), 2.41-2.45 ppm (m, 1H), 2.73 ppm (t, 1H, J=5.62 Hz).

3-Pentylbicyclo[3.2.1]octan-2-one possessed strong sweet, slight anisic, floral, and celery notes.

Example IX

The fragrance properties of the above compounds (i.e., Structures II-VII) were evaluated using an intensity scale of 0 to 3, where 0=none, 1=weak, 2=moderate, 3=strong. Averaged sensory scores were reported in the following:

| No. | Compound | Chemical Name | Odor Profile | Odor Intensity |
|---|---|---|---|---|
| 1 | | 3-propylbicyclo[3.2.1]oct-6-en-2-one (Structure III) | Green, herbaceous, fresh, clean, natural, floral, and woody | 3 |
| 2 | | 3-butylbicyclo[3.2.1]oct-6-en-2-one (Structure V) | Fruity, green, herbal, and celery | 3 |
| 3 | | 3-butylbicyclo[3.2.1]octan-2-one (Structure VI) | Coconut, lactonic, woody, minty, jasmine cis like, anisic, and tuberose | 3 |
| 4 | | 3-pentylbicyclo[3.2.1]oct-6-en-2-one (Structure VII) | Anisic, fruity, spicy, mossy, herbal, and celery | 3 |
| 5 | | 3-pentylbicyclo[3.2.1]octan-2-one (Structure VIII) | Sweet, slight anisic, floral, and celery | 3 |
| 6 | | 3-hexylbicyclo[3.2.1]oct-6-en-2-one | Fruity, floral, sweet, and aldehydic | 1 |
| 7 | | 3-heptylbicyclo[3.2.1]oct-6-en-2-one | Weak, methyl sal like, slight fruity | 1 |

Example IX

Continued

Compound No.s. 1-5 (i.e., Structures III, V, VI, VII, and VIII) exhibited unexpected strong and long-lasting odor, superior to Compound No. 6, which contains a hexyl group, and Compound No. 7, which contains a heptyl group.

Example X

Fragrance formulation containing 3-propylbicyclo[3.2.1]oct-6-en-2-one (Structure III):

| Fragrance Ingredient | Parts by Wt |
| --- | --- |
| Allyl Amyl Glyclolate BHT | 2.00 |
| Amberiff Cryst | 0.30 |
| Bergamot oil Italy MPF "PFG" BLO BHT | 10.00 |
| Citral DMA | 0.50 |
| Citroflex #2 Pfizer | 4.30 |
| Damascone Delta BHT | 0.10 |
| Dihydro Myrcenol | 14.70 |
| Dipropylene Glycol | 5.00 |
| 3-Propylbicyclo[3.2.1]oct-6-en-2-one (Structure III) | 5.00 |
| Geranium Bourbon Type | 0.20 |
| Helional | 0.30 |
| Iso E Super BHT | 5.00 |
| Kharismal | 3.00 |
| Lavandin 4066C WO Color LMR | 0.40 |
| Linalyl Acet Super | 3.00 |
| Lyral BHT | 4.00 |
| Meth Beta Naph Ketone | 0.50 |
| Meth Ionone N BHT | 20.00 |
| Muguesia | 0.20 |
| Nebulone (ELINCS) | 12.00 |
| Peomosa | 1.00 |
| Polysantol (ELINCS) MVB | 1.00 |
| Precyclemone B BHT | 1.00 |
| Undecavertol MVB | 1.00 |
| Vertofix Coeur | 5.00 |
| Total: | 100.00 |

3-Propylbicyclo[3.2.1]oct-6-en-2-one imparts green, herbaceous, fresh, clean, natural, floral, and woody characters to a fragrance formula.

Example XI

Fragrance formulation containing 3-butylbicyclo[3.2.1]oct-6-en-2-one (Structure V):

| Fragrance Ingredient | Parts by Wt |
| --- | --- |
| Acetald DEA | 0.28 |
| Ald C-10 BHA | 0.70 |
| Allyl Amyl Glycolate BHT 0.1% DPG | 1.40 |
| Benz Acet | 0.70 |
| Calone 1% DPG | 1.40 |
| Coumarin | 0.28 |
| Dihydro Myrcenol | 6.99 |
| Dimeth Benz Carb Acet | 6.99 |
| 3-Butylbicyclo[3.2.1]oct-6-en-2-one (Structure V) | 5.00 |
| Eth-2-Meth Buty | 5.59 |
| Eth Vanillin | 0.14 |
| Fleuranil (ELINCS) 10% DPG | 1.40 |
| Galaxolide 50 PCT DPG | 6.99 |
| Galbascone BHT 10% DPG | 0.14 |
| Cyclobutanate (ELINCS) | 0.28 |
| Hexyl Buty | 1.40 |
| Hexyl Cinn Ald BHA/BHT | 6.99 |
| Ionol CP | 0.14 |
| Iso E Super BHT | 6.99 |
| Koavone | 1.40 |
| Mandarin Oil HP "PFG" | 2.80 |
| Mango Ester 0.01 PCT DPG 1% DPG | 1.40 |
| Meth Anth (USDEA) | 0.70 |
| Orange Oil CP "PFG" | 2.80 |
| Undecalactone Gamma Coeur | 1.40 |
| Phenyl Acet | 4.20 |
| Vertoliff | 6.99 |
| Trisamber (ELINCS) 1% DPG | 0.70 |
| Nebulone (ELINCS) | 6.99 |
| Undecavertol MVB | 2.69 |
| Vivaldie (ELINCS) | 0.14 |
| Verdox | 13.99 |
| Total: | 100.00 |

3-Butylbicyclo[3.2.1]oct-6-en-2-one imparts fruity, green, herbal, and celery characters to a fragrance formula.

Example XII

Fragrance formulation containing 3-pentylbicyclo[3.2.1]oct-6-en-2-one (Structure VII):

| Fragrance Ingredient | Parts by Wt |
| --- | --- |
| Acalea BHT/BHA | 3.70 |
| Ald C-8 BHT | 0.14 |
| Applelide (ELINCS) Stabiliff | 6.89 |
| Benz Acet | 3.45 |
| Benz Alc | 6.89 |
| Benz Prop | 3.45 |
| Citronellol Coeur | 6.89 |
| Cyclaprop | 1.03 |
| Cyclemax | 0.69 |
| Dimeth Benz Carb Buty | 8.27 |
| 3-Pentylbicyclo[3.2.1]oct-6-en-2-one (Structure VII) | 5.00 |
| Eth Caproate | 0.69 |
| Eth Vanillin | 0.07 |
| Eth-2-Meth Buty | 0.14 |
| Floralozone | 1.38 |
| Geranyl Acet Pure | 2.07 |
| Helional | 0.14 |
| Hexalon BHT | 0.69 |
| Hexenyl Sal, Cis-3 | 0.28 |
| Hexyl Cinn Ald BHA/BHT | 4.13 |
| Hexyl Sal | 0.07 |
| Iso Cyclemone E BHT | 0.41 |
| Kharismal | 4.35 |
| Lilial | 6.89 |
| Linalool Syn | 5.51 |
| Linalyl Acet | 1.38 |
| Meth Cinnamate | 0.69 |
| Meth Ionone Alpha Extra BHT | 0.34 |
| Muguesia | 2.07 |
| Nerol Coeur | 3.45 |
| Neryl Acet A | 0.14 |
| Ocimene BHT | 0.07 |
| Orange Oil Nova Decol LMR | 2.76 |
| Phen Eth Alc White Extra | 1.72 |
| Styralyl Acet | 0.07 |
| Terpineol Coeur | 1.38 |
| Undecalactone Gamma Coeur | 0.69 |

-continued

| Fragrance Ingredient | Parts by Wt |
| --- | --- |
| Verdox | 5.17 |
| Vertenex | 6.85 |
| Total: | 100.00 |

3-Pentylbicyclo[3.2.1]oct-6-en-2-one imparts anisic, fruity, spicy, mossy, herbal, and celery characters to a fragrance formula.

What is claimed is:
1. A compound, 3-butylbicyclo[3.2.1]octan-2-one.
2. A compound, 3-pentylbicyclo[3.2.1]octan-2-one.

* * * * *